United States Patent
Locke et al.

(10) Patent No.: US 10,576,189 B2
(45) Date of Patent: Mar. 3, 2020

(54) SYSTEMS AND METHODS FOR TREATING A TISSUE SITE WITH REDUCED PRESSURE INVOLVING A REDUCED-PRESSURE INTERFACE HAVING A CUTTING ELEMENT

(71) Applicant: KCI Licensing, Inc., San Antonio, TX (US)

(72) Inventors: Christopher Brian Locke, Bournemouth (GB); Timothy Mark Robinson, Shillingstone (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 197 days.

(21) Appl. No.: 15/842,274

(22) Filed: Dec. 14, 2017

(65) Prior Publication Data
US 2018/0104394 A1 Apr. 19, 2018

Related U.S. Application Data

(63) Continuation of application No. 14/276,853, filed on May 13, 2014, now Pat. No. 9,878,077, which is a
(Continued)

(51) Int. Cl.
*A61M 1/00* (2006.01)
*A61F 13/00* (2006.01)
*A61M 25/00* (2006.01)

(52) U.S. Cl.
CPC ..... *A61M 1/0088* (2013.01); *A61F 13/00068* (2013.01); *A61M 1/00* (2013.01);
(Continued)

(58) Field of Classification Search
CPC .. A61M 1/0031; A61M 1/0088; A61M 27/00; A61M 2205/3344; A61F 13/00063;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Benjamin J Klein

(57) ABSTRACT

Systems and methods for a reduced-pressure interface for providing reduced pressure through a sealing member to a distribution manifold includes a housing having a flange portion and a cavity wall portion such that the cavity wall portion forms a cavity having a tissue-facing cavity opening. A conduit port is coupled to the cavity wall and has a conduit aperture, such that the conduit port is adapted to receive a reduced-pressure delivery conduit. An attachment device is coupled to a tissue-facing side of the flange portion of the housing such that the attachment device couples the housing to the sealing member. Additionally, a cutting element is at least temporarily coupled to the housing proximate to the tissue-facing cavity opening such that the cutting element is adapted to form an aperture in the sealing member when the
(Continued)

cutting element is driven into the sealing member with a driving force.

33 Claims, 9 Drawing Sheets

Related U.S. Application Data continuation of application No. 13/554,620, filed on Jul. 20, 2012, now Pat. No. 8,758,328.

(60) Provisional application No. 61/511,827, filed on Jul. 26, 2011, provisional application No. 61/511,840, filed on Jul. 26, 2011.

(52) U.S. Cl.
CPC .......... *A61M 1/0025* (2014.02); *A61M 25/00* (2013.01); *A61F 2013/0054* (2013.01); *A61F 2013/00174* (2013.01); *A61F 2013/00536* (2013.01); *A61M 2205/3344* (2013.01)

(58) Field of Classification Search
CPC ................ A61F 13/00068; A61F 13/02; A61F 13/0216; A61F 2013/00174; A61F 2013/00412; A61F 2013/00536; A61F 2013/0054; A61F 2013/00927
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,322,695 A | 6/1994 | Shah et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carlon | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,562,014 B2 * | 5/2003 | Lin ................ | A61B 5/14532 600/562 |
| 6,814,079 B2 | 11/2004 | Heaton et al. | |
| 7,815,616 B2 | 10/2010 | Boehringer et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,758,328 B2 | 6/2014 | Locke et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,023,012 B2 | 5/2015 | Tout et al. | |
| 9,198,801 B2 | 12/2015 | Weston | |
| 9,211,365 B2 | 12/2015 | Weston | |
| 9,289,542 B2 | 3/2016 | Blott et al. | |

(56) References Cited

U.S. PATENT DOCUMENTS

| | | | |
|---|---|---|---|
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2004/0064132 | A1 | 4/2004 | Boehringer et al. |
| 2005/0085795 | A1 | 4/2005 | Lockwood et al. |
| 2007/0066946 | A1 | 3/2007 | Haggstrom et al. |
| 2009/0270620 | A1 | 10/2009 | Ini et al. |
| 2009/0270820 | A1* | 10/2009 | Johnson ............ A61F 13/00063 604/290 |
| 2010/0137775 | A1 | 6/2010 | Hu et al. |
| 2010/0228206 | A1 | 9/2010 | Larsson |
| 2011/0092927 | A1 | 4/2011 | Wilkes et al. |
| 2011/0282309 | A1 | 11/2011 | Adie et al. |
| 2012/0116334 | A1* | 5/2012 | Albert ..................... A61F 13/02 604/319 |
| 2014/0163491 | A1 | 6/2014 | Schuessler et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 03073970 A1 | 9/2003 |
| WO | 2007030598 A2 | 3/2007 |
| WO | 2009/070905 A1 | 6/2009 |
| WO | 2010068502 A1 | 6/2010 |
| WO | 2010094957 A1 | 8/2010 |
| WO | 2011087871 A2 | 7/2011 |

OTHER PUBLICATIONS

Susan Mendez-Eatmen, RN; "When wounds Won't Heal" RN Jan. 1998, vol. 61 (1); Medical Economics company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

A Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin

(56) References Cited

OTHER PUBLICATIONS (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for corresponding PCT/US2012/047736, dated Oct. 26, 2012.

International Search Report and Written Opinion for corresponding PCT/US2012/047733, dated Oct. 26, 2012.

Notice of Rejection corresponding to JP2104-52219 dated May 17, 2016.

Canadian Examiner's Report corresponding to Application No. 2843317, dated May 18, 2018.

Canadian Examination Report Corresponding to Application No. 2841811, dated Jun. 4, 2019.

* cited by examiner

SYSTEMS AND METHODS FOR TREATING A TISSUE SITE WITH REDUCED PRESSURE INVOLVING A REDUCED-PRESSURE INTERFACE HAVING A CUTTING ELEMENT

RELATED APPLICATIONS

This application is a continuation of U.S. application Ser. No. 14/276,853, filed May 13, 2014, which is a continuation of U.S. application Ser. No. 13/554,620, filed Jul. 20, 2012, now U.S. Pat. No. 8,758,328, which claims the benefit, under 35 USC § 119(e), of the filing of U.S. Provisional Patent Application Ser. No. 61/511,840, entitled "Systems and Methods for Treating a Tissue Site with Reduced Pressure Involving a Reduced-Pressure Interface having a Cutting Element," filed Jul. 26, 2011, and U.S. Provisional Patent Application Ser. No. 61/511,827, entitled "Systems and Methods for Treating a Tissue Site with Reduced Pressure Involving a Reduced-Pressure Interface having a Multi-Lumen Conduit for Contacting a Manifold," filed Jul. 26, 2011, which is incorporated herein by reference for all purposes.

BACKGROUND

The present disclosure relates generally to medical treatment systems and, more particularly, but not by way of limitation, to systems, methods, and apparatuses for treating a tissue site with reduced pressure involving a reduced-pressure interface having a cutting element.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a manifold device. The porous pad contains cells or pores distributes reduced pressure to the tissue and channel fluids that are drawn from the tissue.

SUMMARY

According to an illustrative embodiment a reduced-pressure interface for providing reduced pressure through a sealing member to a distribution manifold includes a housing having a flange portion and a cavity wall portion such that the cavity wall portion forms a cavity having a tissue-facing cavity opening. A conduit port is coupled to the cavity wall and has a conduit aperture, such that the conduit port is adapted to receive a reduced-pressure delivery conduit. An attachment device is coupled to a tissue-facing side of the flange portion of the housing such that the attachment device couples the housing to the sealing member. Additionally, a cutting element is at least temporarily coupled to the housing proximate to the tissue-facing cavity opening such that the cutting element is adapted to form an aperture in the sealing member when the cutting element is driven into the sealing member with a driving force.

According to another illustrative embodiment a system for treating a tissue site on a patient with reduced pressure includes a distribution manifold for placing proximate to the tissue site, a sealing member for covering the distribution manifold and a portion of intact epidermis of the patient to form a sealed space, a reduced-pressure interface for providing reduced pressure through the sealing member to the distribution manifold, a reduced-pressure source, and a reduced-pressure delivery conduit for fluidly coupling the reduced-pressure source to the reduced-pressure interface. The reduced-pressure interface includes a housing having a flange portion and a cavity wall portion such that the cavity wall portion forms a cavity having a tissue-facing cavity opening, a conduit port coupled to the cavity wall and having a conduit aperture such that the conduit port is adapted to receive the reduced-pressure delivery conduit, an attachment device coupled to a tissue-facing side of the flange portion of the housing such that the attachment device couples the housing to the sealing member, and a cutting element at least temporarily coupled to the housing proximate to the tissue-facing cavity opening. The cutting element is adapted to form an aperture in the sealing member when the cutting element is driven into the sealing member with a driving force.

According to another illustrative embodiment a method for treating a tissue site on a patient with reduced pressure includes disposing a distribution manifold proximate to the tissue site and covering the distribution manifold and a portion of intact epidermis of the patient with a sealing member to form a sealed space in which the distribution manifold is disposed. The sealing member has a first side and a second, tissue-facing side. The method further includes providing a reduced-pressure source, coupling a reduced-pressure interface proximate to the first side of the sealing member, and fluidly coupling a reduced-pressure delivery conduit between the reduced pressure source and the reduced-pressure interface. The reduced-pressure interface includes a housing having a wall portion such that the wall portion forms a cavity having a tissue-facing cavity opening, a conduit port coupled to the cavity wall for receiving the reduced-pressure delivery conduit, an attachment device for coupling the reduced-pressure interface to the sealing member, and a cutting element at least temporarily coupled to the housing proximate to the tissue-facing cavity opening such that the cutting element is adapted to perforate the sealing member when the cutting element is driven into the sealing member with a driving force. The method also includes applying a driving force to the reduced-pressure interface of sufficient strength to cause the cutting element to perforate the sealing member.

According to yet another illustrative embodiment, an interface for providing reduced pressure through a drape to a manifold includes a housing having a flange portion and a cavity wall portion. The cavity wall portion forms a cavity and a cavity wall aperture is formed within the cavity wall portion for receiving a tube. The interface further includes a coupler positioned on a tissue-facing side of the flange portion of the housing for attaching the housing to the drape and a protrusion coupled to the housing proximate to the flange portion. The protrusion extends beyond the tissue-facing side of the flange portion of the housing and is configured to form an aperture in the drape when the protrusion is driven into the drape with the reduced pressure.

According to another illustrative embodiment, a system for treating a wound with reduced pressure includes a manifold for positioning adjacent the wound, a drape for covering the manifold and a portion of intact epidermis of the patient to form a sealed space, a reduced-pressure interface for providing reduced pressure through the drape to the manifold, a reduced-pressure source, and a conduit for fluidly coupling the reduced-pressure source to the reduced-pressure interface. The reduced-pressure interface includes a housing having a flange portion and a cavity wall portion. The cavity wall portion forms a cavity and a cavity wall aperture is formed within the cavity wall portion for receiving a tube. The reduced-pressure interface further includes a coupler positioned on a tissue-facing side of the flange portion of the housing for attaching the housing to the drape and a protrusion coupled to the housing proximate to the flange portion. The protrusion extends beyond the tissue-facing side of the flange portion of the housing and is configured to form an aperture in the drape when the protrusion is driven into the drape with the reduced pressure.

In another illustrative embodiment, a method for treating a wound on a patient with reduced pressure includes disposing a manifold proximate to the wound, covering the manifold and a portion of intact epidermis of the patient with a drape to form a sealed space in which the manifold is disposed. The drape has a first side and a second, tissue-facing side. The method further includes providing a reduced-pressure source, coupling a reduced-pressure interface proximate to the first side of the drape, and fluidly coupling a tube between the reduced-pressure source and the reduced-pressure interface. The reduced-pressure interface includes a housing having a flange portion and a cavity wall portion. The cavity wall portion forms a cavity and a cavity wall aperture is formed within the cavity wall portion for receiving a tube. The reduced-pressure interface further includes a coupler positioned on a tissue-facing side of the flange portion of the housing for attaching the housing to the drape and a protrusion coupled to the housing proximate to the flange portion. The protrusion extends beyond the tissue-facing side of the flange portion of the housing and is configured to form an aperture in the drape when the protrusion is driven into the drape with a driving force. The method further includes applying the driving force to the reduced-pressure interface of sufficient strength to cause the protrusion to perforate the drape.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Unless otherwise indicated, values of pressure stated herein are gauge pressures. References to increases in reduced pressure typically refer to a decrease in absolute pressure, and decreases in reduced pressure typically refer to an increase in absolute pressure.

Figure 1:
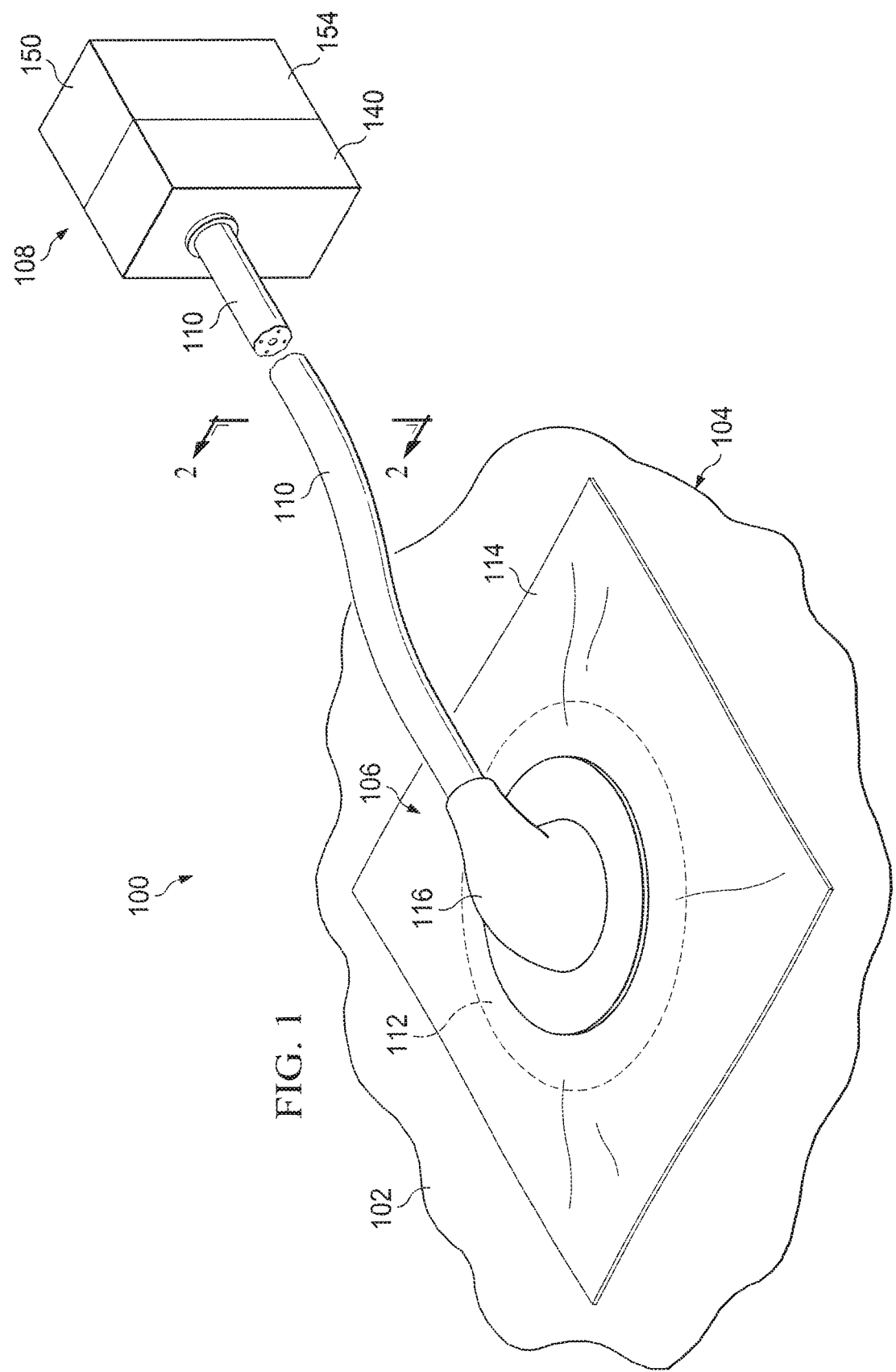
FIG. 1 is a schematic perspective view of an illustrative embodiment of a system for treating a tissue site with reduced pressure.
Figure 2:
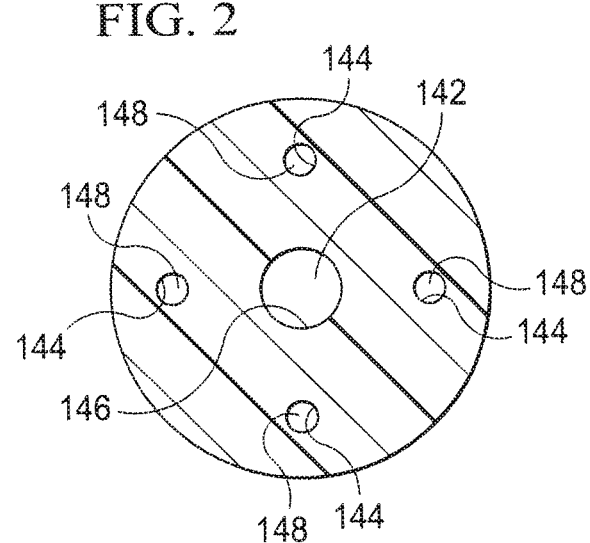
FIG. 2 is a schematic, cross-sectional view of an illustrative embodiment of a multi-lumen conduit of the system shown in FIG. 1 taken along line 2-2.
Figure 3:
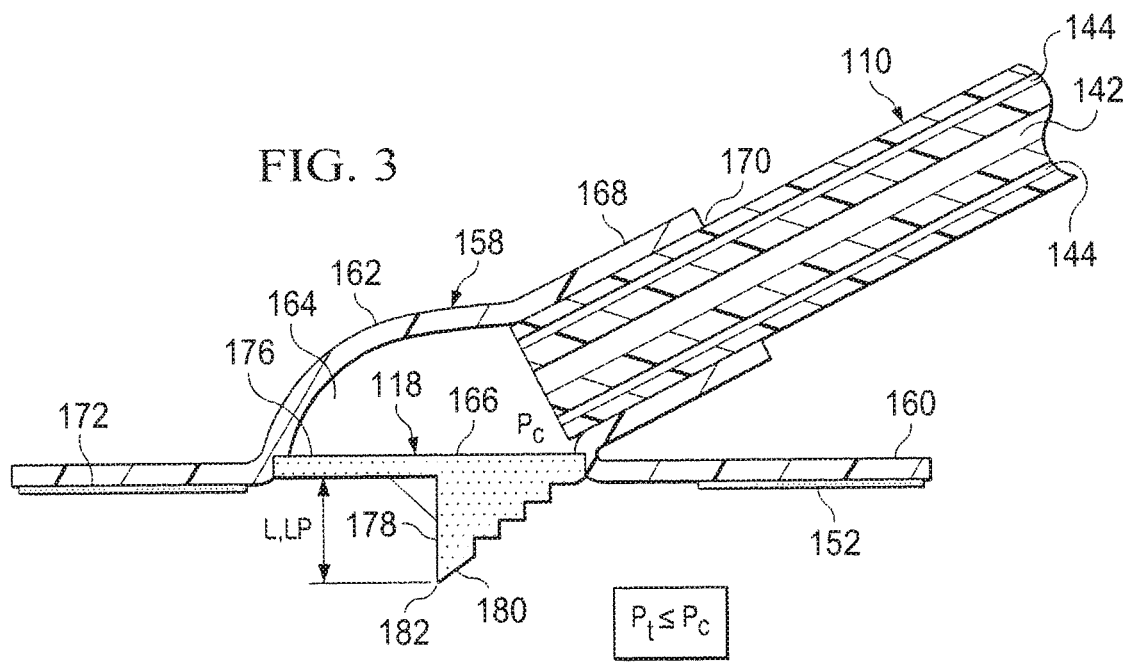
FIG. 3 is a schematic, cross-sectional view of one illustrative embodiment of a reduced-pressure interface having a cutting element for use as part of a system for treating a tissue site with reduced pressure.
Figure 4:
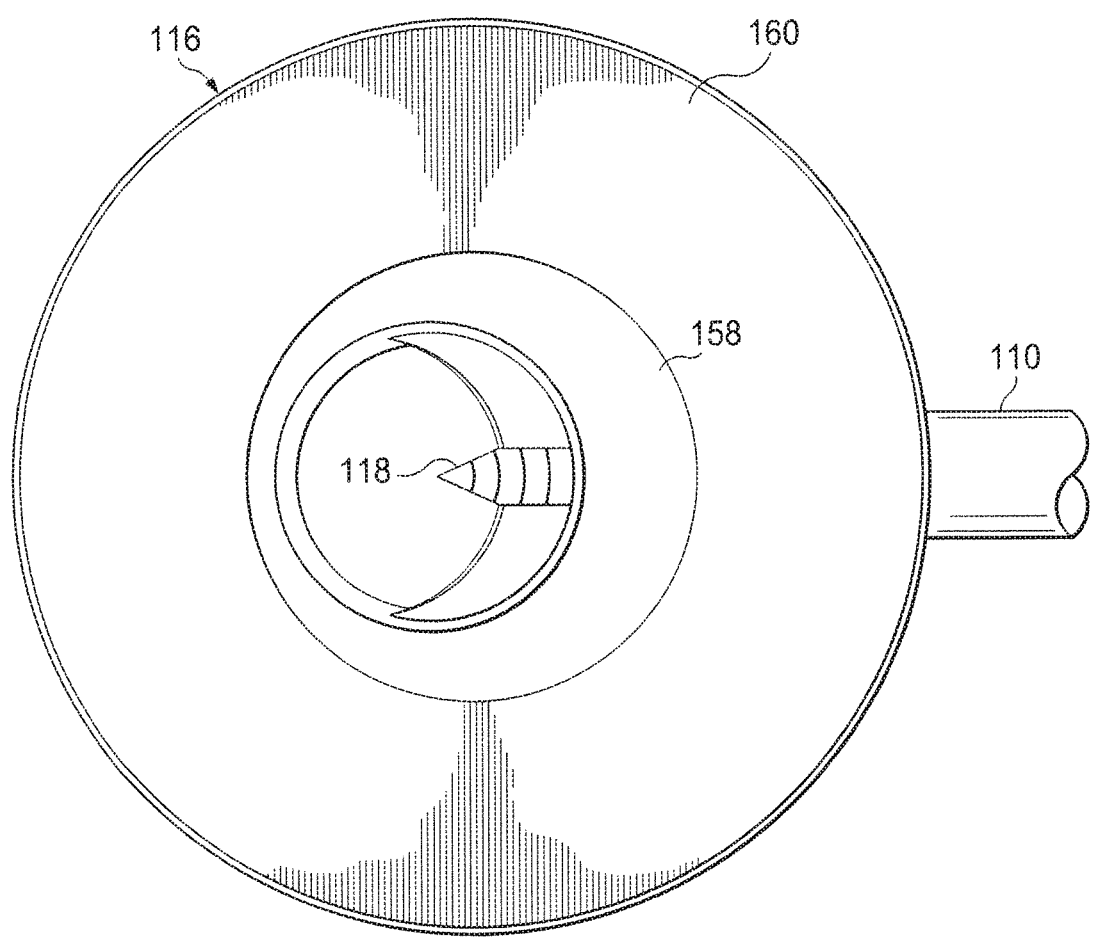
FIG. 4 is a schematic, bottom view of the reduced-pressure interface of FIG. 3.

Referring now to the drawings and initially to FIGS. 1-5C, and specifically to FIGS. 1 and 3, a system 100 for treating a tissue site 102 on a patient 104 with reduced pressure is presented. The system 100 includes a reduced-pressure dressing 106 for disposing proximate the tissue site 102. The system 100 also includes a reduced-pressure treatment unit 108 fluidly connected to the reduced-pressure dressing 106 through a reduced-pressure delivery conduit 110 for applying reduced pressure to the tissue site 102. The reduced-pressure dressing 106 may further include a distribution manifold 112, a sealing member 114, and a reduced-pressure interface 116. The reduced-pressure interface 116 includes a cutting element 118 adapted to form an aperture 120 (see FIG. 5B) in the sealing member 114. Including the cutting element 118 on the reduced-pressure interface 116 provides a number of potential benefits. The benefits may include ease of application and the reduction of error when forming the aperture 120. In a non-limiting example, errors in (1) positioning the aperture 120 on the dressing, (2) sizing of the aperture 120, and (3) the formation of the aperture 120 may be reduced. Incorrectly forming the aperture 120 may leave portions of the sealing member 114 in a position that can block the aperture 120 when reduced pressure is applied.

The system 100 may be used with various different types of tissue sites 102. The tissue site 102 may be a wound 122 or wound cavity. As shown in at least FIGS. 5A-5C, the tissue site 102 or wound 122, may be through an epidermis 124 and into a subcutaneous tissue 126 or any other tissue. The tissue site 102 may be the bodily tissue of any human, animal, or other organism, including bone tissue, adipose tissue, muscle tissue, dermal tissue, vascular tissue, connective tissue, cartilage, tendons, ligaments, body cavity or any other tissue. Treatment of the tissue site 102 may include removal of fluids, e.g., exudate or ascites.

Referring still to FIGS. 1-5C, the distribution manifold 112 is proximate the tissue site 102 and has a first side 128 and a second, tissue-facing side 130. The term "distribution manifold" as used herein generally refers to a substance or structure that is provided to assist in applying reduced pressure to, delivering fluids to, or removing fluids from the tissue site 102. The distribution manifold 112 typically includes a plurality of flow channels or pathways that distribute fluids provided to and removed from the tissue site 102 around the distribution manifold 112. In one illustrative embodiment, the flow channels or pathways are interconnected to improve distribution of fluids provided or removed from the tissue site 102. The distribution manifold 112 may be a biocompatible material that is capable of being placed in contact with the tissue site 102 and distributing reduced pressure to the tissue site 102. Examples of the distribution manifold 112 may include, without limitation, devices that have structural elements arranged to form flow channels, such as, for example, cellular foam, open-cell foam, porous tissue collections, liquids, gels, and foams that include, or cure to include, flow channels. The distribution manifold 112 may be porous and may be made from foam, gauze, felted mat, or any other material suited to a particular biological application. In one embodiment, the distribution manifold 112 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the distribution manifold 112 may also be used to distribute fluids such as medications, antibacterials, growth factors, and various solutions to the tissue site 102. Other layers may be included in or on the distribution manifold 112, such as absorptive materials, wicking materials, hydrophobic materials, and hydrophilic materials.

In one illustrative the distribution manifold 112 may be constructed from bioresorbable materials that do not have to be removed from a patient's body following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 112 may further serve as a scaffold for new cell-growth, or a scaffold material may be used in conjunction with the distribution manifold 112 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The distribution manifold 112 may be covered by the sealing member 114, which may also be referred to as a drape. The sealing member 114 forms a sealed space 132 over the tissue site 102. The sealing member 114 has a first side 134, and a second, tissue-facing side 136. The sealing member 114 may be any material that provides a fluid seal. "Fluid seal," or "seal," means a seal adequate to maintain reduced pressure at a desired site given the particular reduced-pressure source or subsystem involved. The sealing member 114 may, for example, be an impermeable or semi-permeable, elastomeric material. "Elastomeric" means having the properties of an elastomer. Elastomer generally refers to a polymeric material that has rubber-like properties. More specifically, most elastomers have ultimate elongations greater than 100% and a significant amount of resilience. The resilience of a material refers to the material's ability to recover from an elastic deformation. Elastomers that are relatively less resilient may also be used as these elastomers are more likely to tear when faced with the cutting element 118. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of dressing sealing member materials include a silicone drape, 3M Tegaderm® drape, polyurethane (PU) drape such as one available from Avery Dennison Corporation of Pasadena, Calif. An additional, specific non-limiting example of a dressing sealing member material includes a 30 μm matt polyurethane film such as the Inspire™ 2317 manufactured by Exopack™ Advanced Coatings of Matthews, N.C.

An attachment device 134 may be used to hold the sealing member 114 against a portion of the patient's intact epidermis 124 or another layer, such as a gasket or additional sealing member. The attachment device 134 may take numerous forms. For example, the attachment device 134 may be a medically acceptable adhesive, such as a pressure-sensitive adhesive, that extends about a periphery or all of the sealing member 114. The attachment device 134 may also be a sealing ring or other device. The attachment device 134 is disposed on the second, tissue-facing side of the sealing member 114. Before use, the attachment device 134 may be covered by a release liner (not shown).

The reduced-pressure interface 116 may be positioned adjacent to or coupled to the sealing member 114 to provide fluid access to the distribution manifold 112. Another attachment device 138 similar to the attachment device 134 may be used to hold the reduced-pressure interface 116 against the sealing member 114. The reduced-pressure delivery conduit 110 fluidly couples the reduced-pressure treatment unit 108 and the reduced-pressure interface 116. The reduced-pressure interface 116 allows the reduced pressure to be delivered to the tissue site 102. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

As shown, the reduced-pressure delivery conduit 110 is a multi-lumen conduit. It should be understood, however, that the reduced-pressure delivery conduit 110 may be in many forms and may comprise a single lumen. The reduced-pressure delivery conduit 110 may include a primary lumen 142 and at least one sensing lumen 144. In one illustrative embodiment the primary lumen 142 is a central lumen 146 and the at least one sensing lumen 144 is one or more peripheral lumens 148. The primary lumen 142 and the at least one sensing lumen 144 are adapted to maintain fluid isolation between the primary lumen 142 and the at least one sensing lumen 144 as the reduced-pressure delivery conduit 110 transports fluids from the reduced-pressure interface 116 to the reduced-pressure treatment unit 108. Liquids or exudates communicated from the distribution manifold 112 through the primary lumen 142 are removed from the reduced-pressure delivery conduit 110 and retained within a liquid-collection chamber (not explicitly shown) in fluid communication with the reduced-pressure treatment unit 108. The at least one sensing lumen 144 fluidly communicates reduced pressure representative of the tissue site 102 to an instrumentation unit 150.

The reduced-pressure treatment unit 108 may include a liquid-collection chamber, or a collection canister, and the instrumentation unit 150 in fluid communication with a reduced-pressure source 140. The instrumentation unit 150 may include a microprocessor 154 adapted to process pressure signals received by the reduced-pressure delivery conduit 110, monitor the pressure signals, and issue alerts according to a pre-determined pressure configuration. The pre-determined pressure configuration may include a pressure set-up pattern of sustained decrease, increase, and relative stability within an application time period as will be described in more detail with respect to FIG. 10 below.

In an illustrative embodiment, the reduced-pressure source 140 is an electrically-driven vacuum pump. In another implementation, the reduced-pressure source 140 may instead be a manually-actuated or manually-charged pump that does not require electrical power. The reduced-pressure source 140 instead may be any other type of reduced pressure pump, or alternatively a wall suction port such as those available in hospitals and other medical facilities. The reduced-pressure source 140 may be housed within or used in conjunction with the reduced-pressure treatment unit 108, which may also include the instrumentation unit 150. The instrumentation unit 150 may include sensors, processing units, alarm indicators, memory, databases, software, display units, and user interfaces that further facilitate the application of reduced pressure treatment to the tissue site 102.

In one example, pressure-detection sensors (not shown) located in the instrumentation unit 150 may be disposed at or near the reduced-pressure source 140. The pressure-detection sensors may receive pressure data, or a pressure signal, from the reduced-pressure interface 116 via the at least one sensing lumen 144 that is dedicated to delivering reduced pressure data to the pressure-detection sensors. The pressure signal or data may be representative of a pressure at a distal end 186 of the at least one sensing lumen 144. The pressure-detection sensors may communicate with a processing unit that monitors and controls the reduced pressure that is delivered by the reduced-pressure source 140. In one embodiment, the pressure-detection sensors communicate with the processing unit to monitor whether the pressure signal follows the pressure set-up pattern. In the event the pressure signal does not follow the pressure set-up pattern within an application time period that may be predetermined, the instrumentation unit 150 provides an indication to a caregiver. The indication may be in the form of a visual or audible alert or alarm. Other indications may be used. In an alternative, but not mutually exclusive, embodiment, the pressure-detection sensors may communicate with the processing unit to monitor whether the pressure signal does follow the pressure set-up pattern within an application time period. In the event the pressure signal does follow the pressure set-up pattern, the instrumentation unit 150 provides an indication to the caregiver. The indication that the pressure set-up pattern has been followed may be different than the indication that the pressure set-up pattern has not been followed.

Referring now primarily to FIGS. 3-5C, an illustrative embodiment of the reduced-pressure interface 116 is presented in more detail. The reduced-pressure interface 116 includes a housing 158, a conduit port 168 coupled to the housing 158, and the attachment device 152 for coupling the reduced-pressure interface 116 to the sealing member 114. The reduced-pressure interface 116 further includes the cutting element 118.

The housing 158 may have a flange portion 160 and a cavity wall portion 162. The cavity wall portion 162 forms a cavity 164 having a tissue-facing cavity opening 166. The conduit port 168 is coupled to or formed as part of the cavity wall portion 162 of the housing 158. The conduit port 168 includes a conduit aperture 170 whereby the conduit port 168 is adapted to receive the reduced-pressure delivery conduit 110. The attachment device 138 may be coupled to a tissue-facing side 172 of the flange portion 160 for coupling the housing 158 to the first side 134 of the sealing member 114. The housing 158 is made of a semi-rigid material that is capable of collapsing under a force such as a driving force 174. In a non-limiting example, the reduced-pressure interface 116, and thus the housing 158, may be made from a plasticized polyvinyl chloride (PVC), polyurethane, cyclic olefin copolymer elastomer, thermoplastic elastomer, poly acrylic, silicone polymer, and polyether block amide copolymer.

The cutting element 118 may be at least temporarily coupled to the housing 158 proximate to the tissue-facing cavity opening 166. The cutting element 118 is adapted to form the aperture 120 in the sealing member 114 when the cutting element 118 is driven into the sealing member 114 with the driving force 174. The driving force 174 may also cause the cutting element 118 to penetrate or cut a portion of the distribution manifold 112. The driving force 174 may be manually applied to an exterior 184 of the reduced-pressure interface 116 causing the housing 158 to collapse and thereby driving or pushing the cutting element 118 into the sealing member 114. In another embodiment, the driving force 174 is applied by applying reduced pressure to the cavity 164 such that a cavity pressure ($P_c$) in the cavity 164 is less than a threshold pressure ($P_t$). When the cavity pressure ($P_c$) is less than the threshold pressure ($P_t$), the cavity wall portion 162 collapses and with continued reduced pressure impacts the cutting element 118 thereby driving a portion of the cutting element 118 through the sealing member 114. The threshold pressure ($P_t$) is at least in part dependent on the type and thickness of the material used for the housing 158. In the event reduced pressure is applied to the cavity 164, a tensile force may be applied to the sealing member 114 causing the sealing member 114 to pull into the cavity 164. This movement further assists with the cutting element 118 moving into the sealing member 114.

In one embodiment, the cutting element 118 includes a base member 176 and a stylus member 178 coupled to the base member 176. The stylus member 178 has a leading edge 180 and is configured to perforate the sealing member 114 to form the aperture 120 in the sealing member 114. In one embodiment, the leading edge 180 is serrated. In another embodiment, the leading edge 180 is serrated or configured to perforate the sealing member 114 orthogonally. The sealing member 114 may be perforated orthogonally to inhibit the cut sealing member 114 from blocking the reduced-pressure delivery conduit 110 during reduced pressure therapy. The base member 176 may be sized and configured to form an interference fit with the tissue-facing cavity opening 166, whereby the cutting element 118 is releasably coupled to the housing 158. Thus, in one embodiment, the cutting element 118 may be removed prior to use if not desired or after perforating the sealing member 114.

The cutting element 118 may have a piercing length ($L_p$) extending the length (L) of the stylus member 178. The length (L) of the stylus member 178 extends from the base member 176 to a tip 182 of the stylus member 178. In one embodiment, the piercing length ($L_p$) is less than 3 centimeters. In another embodiment, the piercing length ($L_p$) is less than 2 centimeters. The distribution manifold 112 may have a thickness greater than T when subject to reduced pressure such that the piercing length ($L_p$) of the cutting element 118 is less than the thickness T, i.e., $L_p$<T. One benefit of the piercing length ($L_p$) being less than the thickness, T, of the distribution manifold 112 under reduced pressure is that the cutting element 118 cannot completely cut through the distribution manifold 112 and reach the tissue site 102.

As previously mentioned, the cutting element 118 may be only temporarily coupled to the housing 158. In one embodiment, the cutting element 118 may be removed by a care giver. In another embodiment, the cutting element 118 may be formed from a liquid soluble material such as a water soluble material adapted to allow the cutting element 118 to dissolve. For example, the water soluble material may include at least one of the following: Polyvinyl alcohol (PVOH), polyvinyl pyrrolidone, hydroxyl and carboxyl modified cellulose, hydroxyl and carboxyl modified acrylics, starch, sugars (sucrose, glucose, fructose), weak acids (tartaric, citric, malic), salts (sodium chloride, sodium carbonate, sodium bicarbonate), polyethylene oxide (PEO), polyethylene glycol (PEG). The cutting element 118 may dissolve as liquids are removed from the tissue site 102. Reduced pressure is applied to the reduced-pressure interface 116 after perforating the sealing member 114 typically causing liquids to be removed from the tissue site 102. After a sufficient amount of time, liquids removed from the tissue site 102 cause the cutting element 118 to substantially dissolve. The cutting element 118 may dissolve within 2 minutes, 5 minutes, 10 minutes, or another time period. As the cutting element 118 is dissolved it is removed by the reduced-pressure delivery conduit 110 with liquids from the tissue site 102. A liquid, e.g., saline solution, may also be introduced through the reduced-pressure delivery conduit 110 or otherwise to dissolve the cutting element 118.

Figure 5A:
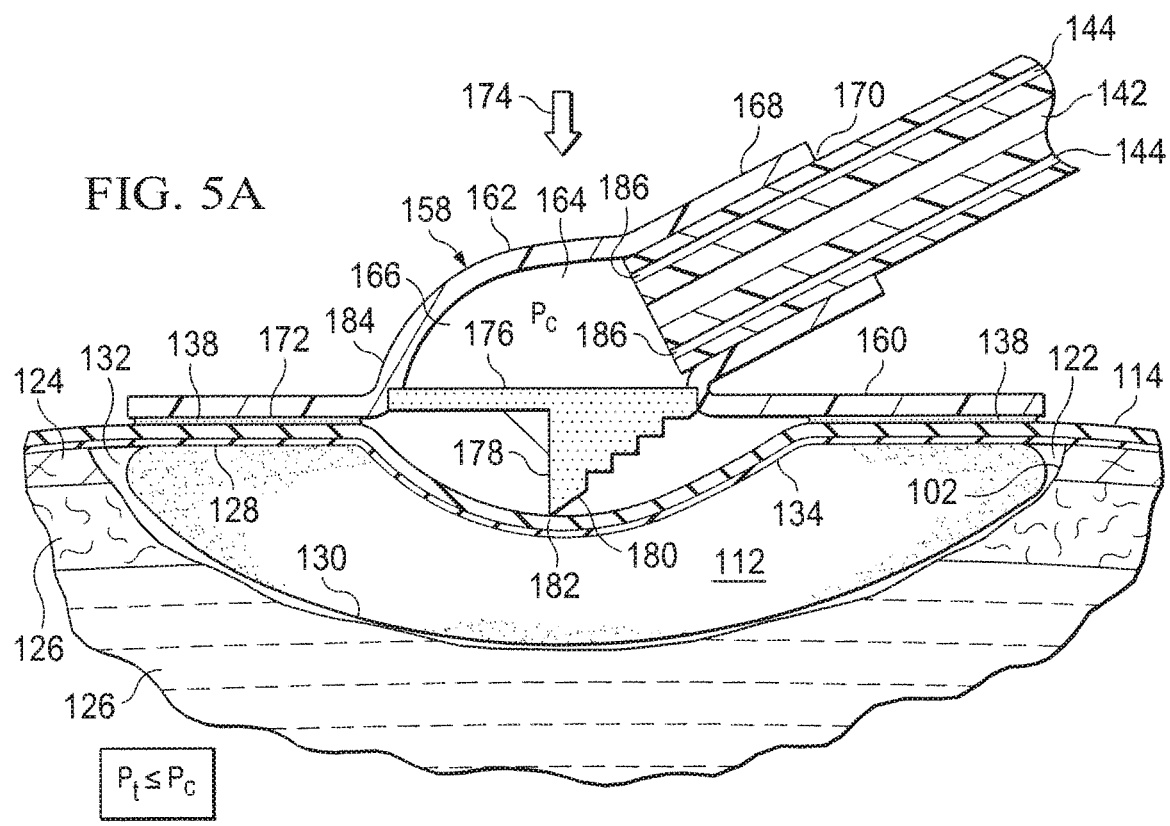
FIG. 5A is a schematic, cross-sectional view of the reduced-pressure interface of FIG. 3 under reduced pressure prior to the cutting element perforating a sealing member.
Figure 5B:
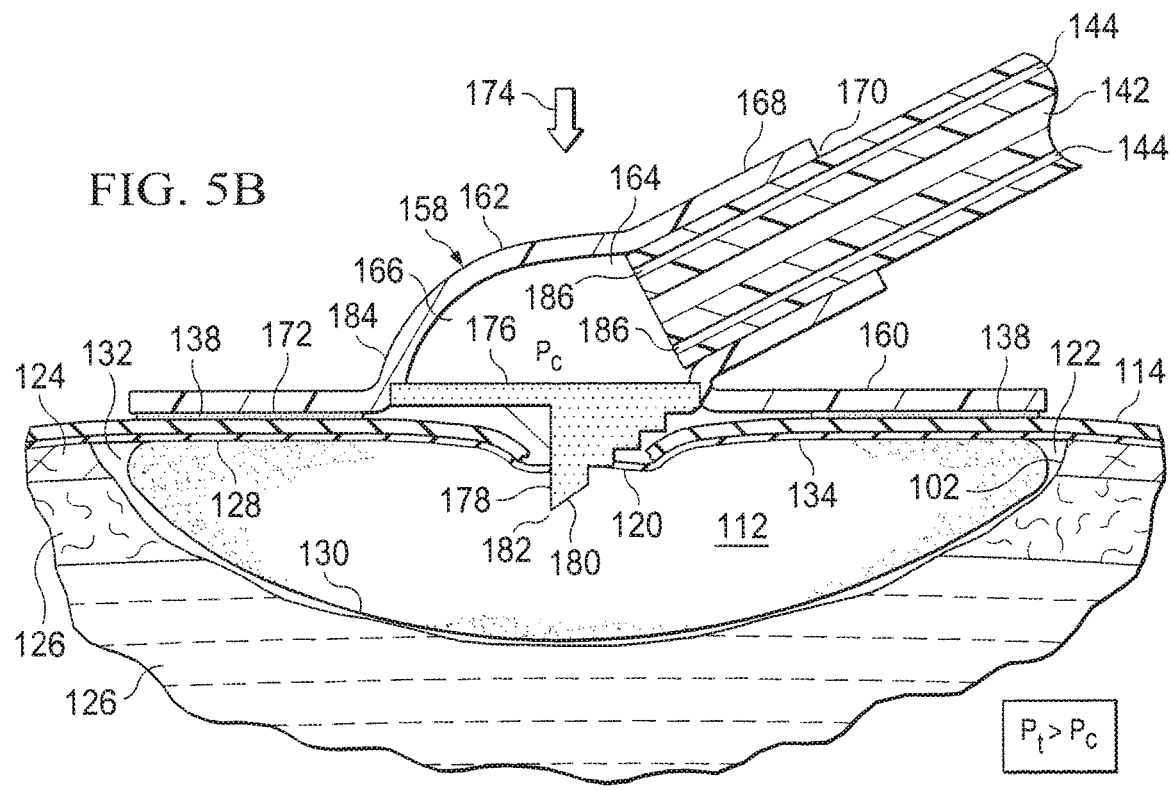
FIG. 5B is another schematic, cross-sectional view of the reduced-pressure interface of FIG. 3 under reduced pressure after the cutting member has perforated the sealing member.
Figure 5C:
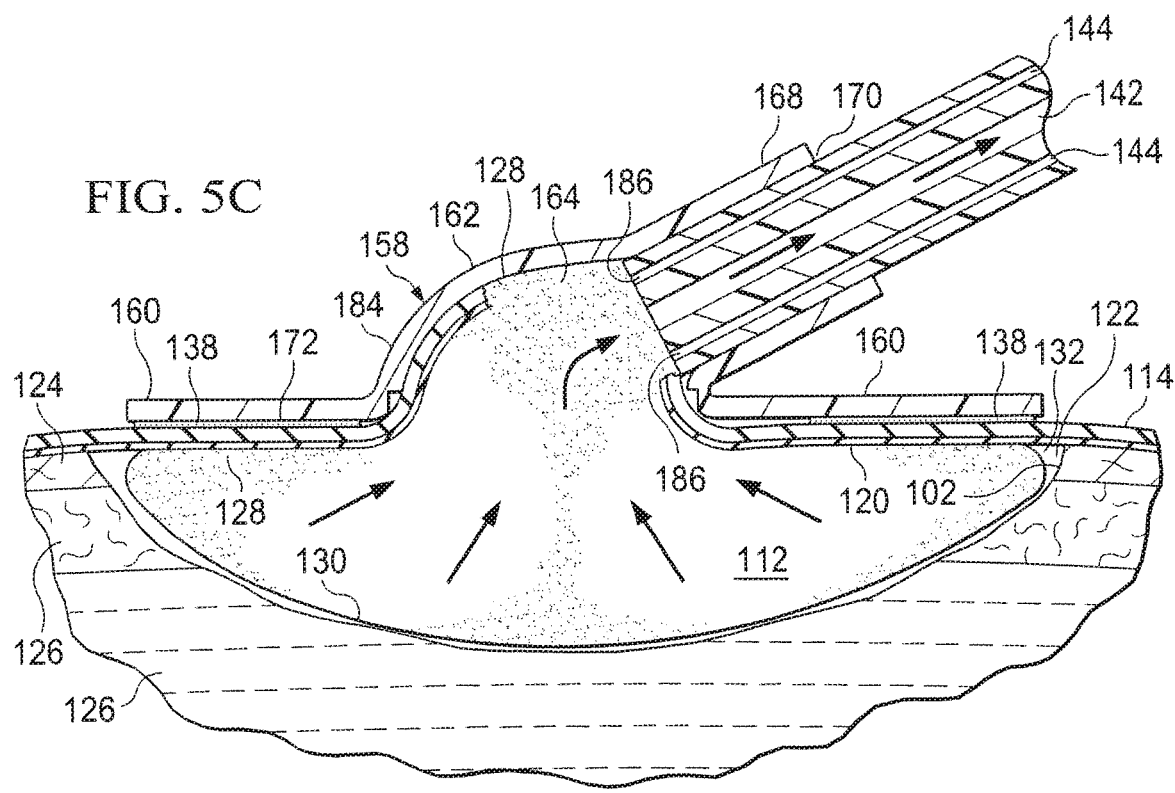
FIG. 5C is another schematic, cross-sectional view of the reduced-pressure interface of FIG. 3 under reduced pressure after the cutting member has perforated the sealing member and the cutting element has been removed.
Figure 6:
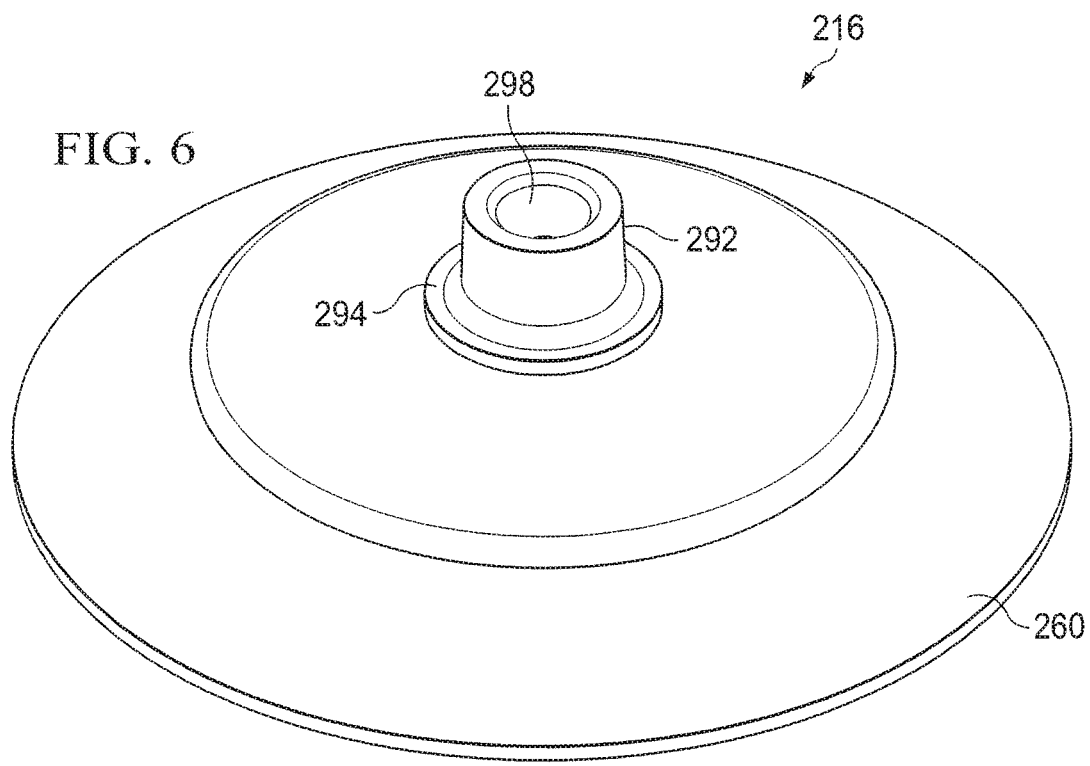
FIG. 6 is a schematic, top perspective view of another illustrative embodiment of a reduced-pressure interface having a cutting element for use as part of a system for treating a tissue site with reduced pressure.
Figure 7:
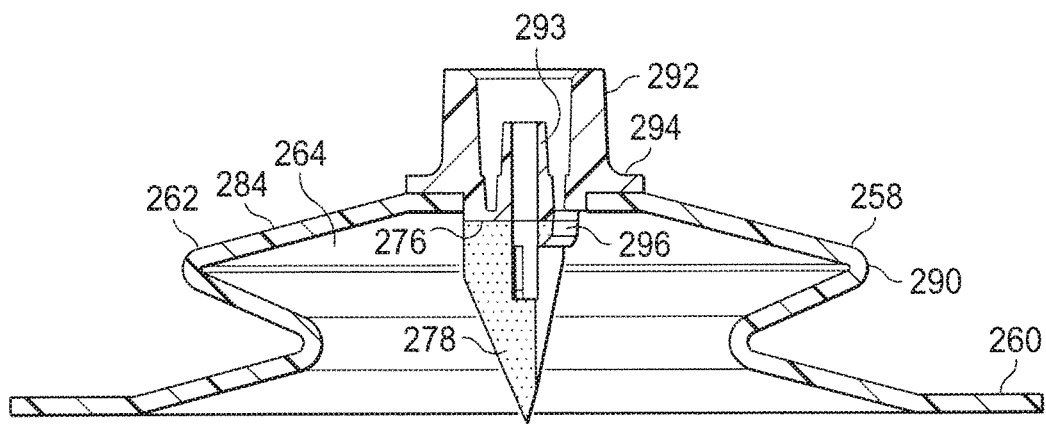
FIG. 7 is a schematic, cross-sectional view of the reduced-pressure interface of FIG. 6.
Figure 8:
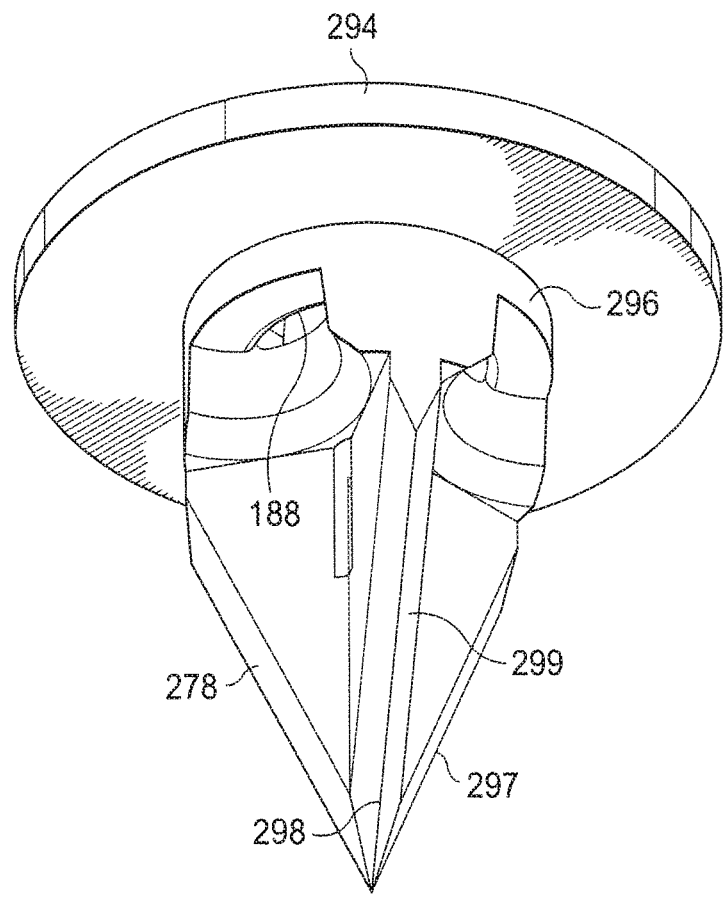
FIG. 8 is a schematic, bottom perspective view of a portion of the reduced-pressure interface of FIG. 6.
Figure 9A:
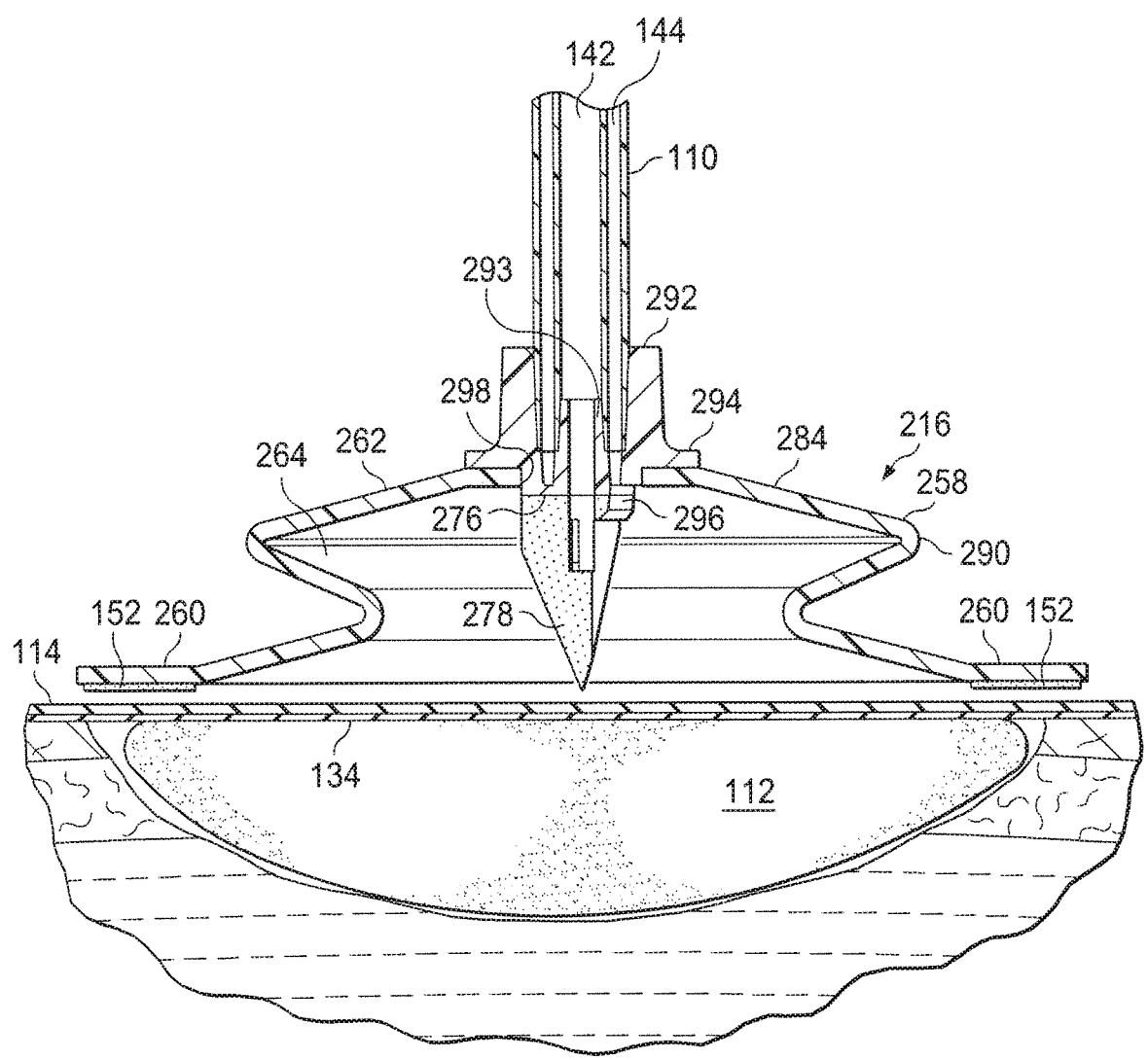
FIG. 9A is a schematic, cross-sectional view of the reduced-pressure interface of FIGS. 6-8 being applied and prior to reduced pressure being supplied.
Figure 9B:
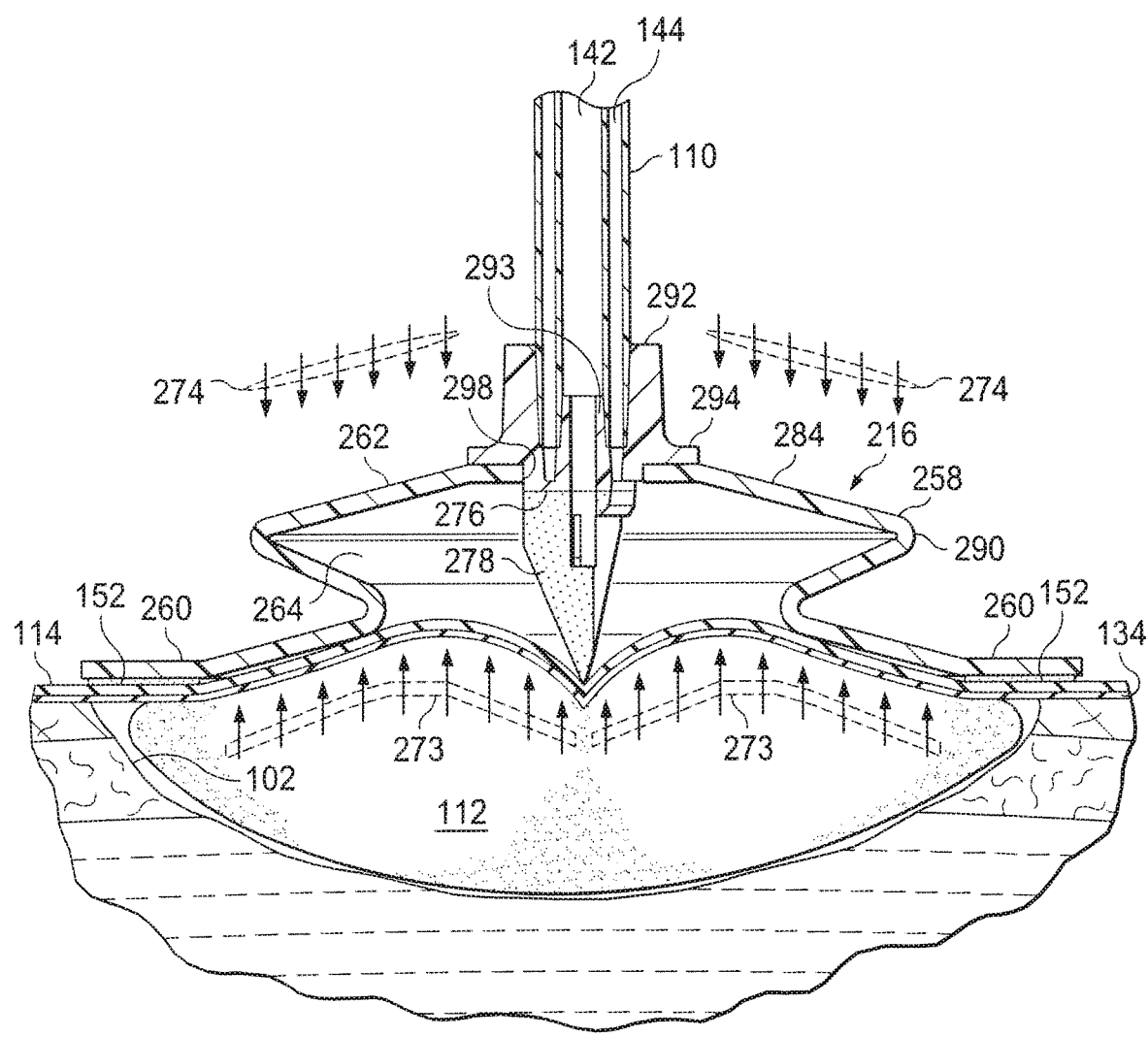
FIG. 9B is a schematic, cross-sectional view of the reduced-pressure interface of FIGS. 6-8 under reduced pressure prior to the cutting element perforating a sealing member.
Figure 9C:
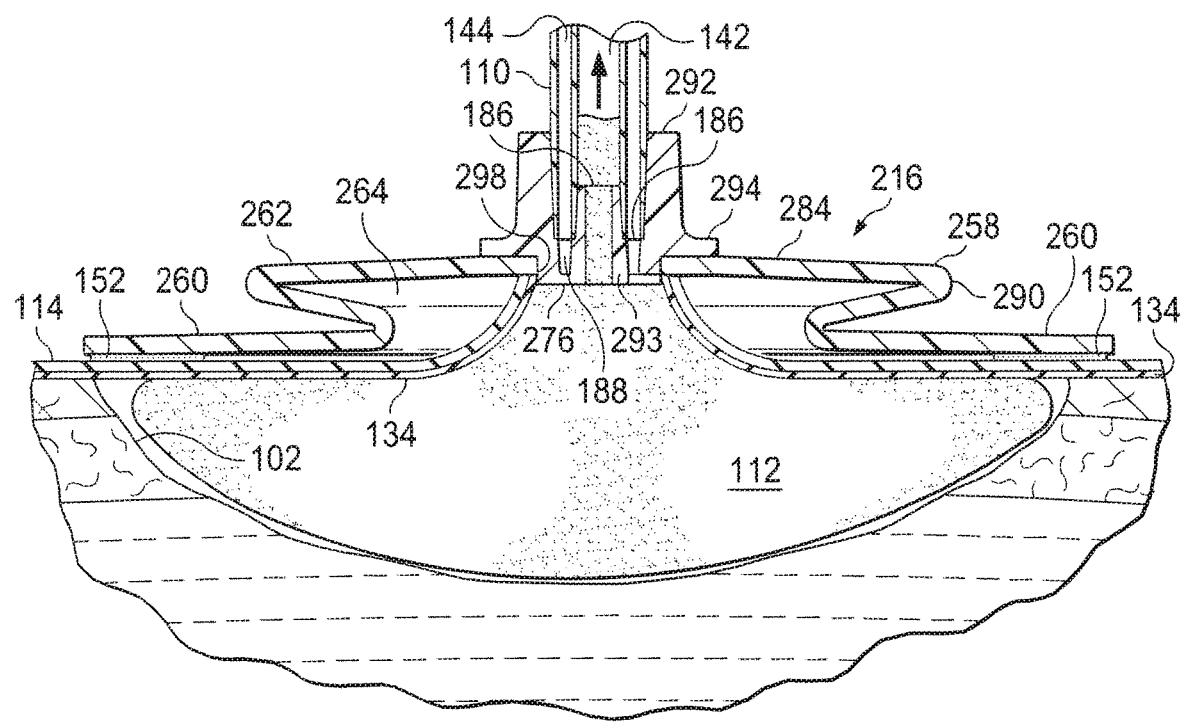
FIG. 9C is a schematic, cross-sectional view of the reduced-pressure interface of FIGS. 6-8 under reduced pressure after the cutting member has perforated the sealing member and the cutting element has been removed.

As shown in FIG. 5C, once the cutting element 118 has substantially dissolved, reduced pressure applied through the reduced-pressure interface 116 creates sufficient reduced pressure in the cavity 164 to pull a portion of the distribution manifold 112 into the cavity 164 such that the distribution manifold 112 abuts a distal end of the reduced-pressure delivery conduit 110 to include a distal aperture 186 of the at least one sensing lumen 144. Allowing the distribution manifold 112 to completely abut the distal end of the reduced-pressure delivery conduit 110 may help ensure fluid isolation between each of the lumens in the reduced-pressure delivery conduit 110. The distribution manifold 112 may provide a barrier between the primary lumen 142 and the at least one sensing lumen 144. Additionally, having the reduced-pressure delivery conduit 110 in direct contact with the distribution manifold 112 may help ensure that there is a constant low velocity liquid flow into the reduced-pressure delivery conduit 110 which may minimize the instance of aerosolized particles being deposited around the at least one sensing lumen 144 and may also provide a filter to liquids entering the at least one sensing lumen 144.

In operation, a caregiver may treat the tissue site 102 on the patient 104 with a method that includes disposing the distribution manifold 112 proximate to the tissue site 102. The distribution manifold 112 and a portion of intact epidermis 124 of the patient 104 is covered with the sealing member 114 to form the sealed space 132 in which the distribution manifold 112 is disposed. The reduced-pressure interface 116 is coupled to the sealing member 114. The reduced-pressure delivery conduit 110 is fluidly coupled on one end to the reduced-pressure source 140 and on the opposing end to the reduced-pressure interface 116. The driving force 174 is then applied to the reduced-pressure interface 116 with sufficient strength to cause the cutting element 118 to perforate (e.g., pierce, tear, cut or otherwise create the aperture 120) the sealing member 114.

In one embodiment, the reduced-pressure interface 116 includes the housing 158 having the wall portion, wherein the wall portion forms the cavity 164 having the tissue-facing cavity opening 166. The housing 158 is formed of a semi-rigid material that collapses when under reduced pressure less than the threshold pressure ($P_t$). The conduit port 168 is coupled to the wall portion of the housing 158. The conduit port 168 is further coupled to the reduced-pressure delivery conduit 110. Reduced pressure is supplied to the reduced-pressure interface 116 through the reduced-pressure delivery conduit 110 and the conduit port 168. When reduced pressure levels in the cavity 164 are less than the threshold pressure ($P_t$), the wall portion collapses under the driving force 174 and impacts the cutting element 118, driving a portion of the cutting element 118 through the sealing member 114 to perforate the sealing member 114.

In one embodiment, in response to the sealing member 114 being perforated, liquid is removed from the tissue site 102 through the reduced-pressure delivery conduit 110. Liquid is removed from the tissue site 102 by virtue of reduced pressure. The liquid causes the cutting element 118 to dissolve. Once the cutting element 118 has substantially dissolved, reduced pressure within the cavity 164 of the reduced-pressure interface 116 causes a portion of the distribution manifold 112 to be pulled into the cavity 164 and abut the reduced-pressure delivery conduit 110. Fluid may then be directly transferred from the distribution manifold 112 to the reduced-pressure delivery conduit 110 without going through an additional medium or open space.

Referring now primarily to FIGS. 6-9C, another illustrative embodiment of a reduced-pressure interface 216 is presented. The reduced-pressure interface 216 is analogous in many respects to the reduced-pressure interface 116 of FIGS. 3-5C. The reduced-pressure interface 216 includes a housing 258 and a cutting element 218. The housing 258 may have a flange portion 260 and a cavity wall portion 262.

The flange portion 260 may be coupled to the sealing member 114 by the attachment device 138. The cavity wall portion 262 is collapsible under reduced pressure. The cavity wall portion 262 may include a bellows configuration 290 for permitting the cavity wall portion 262 to collapse when a cavity 164 pressure ($P_c$) inside a cavity 264 is less than a threshold pressure ($P_t$) on an absolute pressure side.

The cutting element 218 may include a conduit adapter 292, an adapter flange 294, a tube extension 296, a base member 276, and a stylus member 278. The conduit adapter 292 is configured to receive the reduced-pressure delivery conduit 110 to provide fluid communication between the reduced-pressure treatment unit 108 and the tissue site 102. The conduit adapter 292 includes a protrusion 293 for engaging the primary lumen 142 of the reduced-pressure delivery conduit 110. The protrusion 293 may be sized and configured to extend into the primary lumen 142 and to form an interference fit. The protrusion 293 may help maintain fluid isolation between the primary lumen 142 and the at least one sensing lumen 144. The adapter flange 294 is positioned on an exterior 284 of the cavity wall portion 262. The tube extension 296 is connected to the adapter flange 294 and is sized and configured to mate with a conduit aperture 298. The tube extension 296 is further configured to extend through the conduit aperture 298. In a specific, non-limiting example, the conduit adapter 292, the adapter flange 294, and the tube extension 296 may be formed from materials to include plasticized polyvinyl chloride (PVC), polyurethane, cyclic olefin copolymer elastomer, thermoplastic elastomer, poly acrylic, silicone polymer, and polyether block amide copolymer.

The base member 276 may be at least temporarily coupled to the tube extension 296. The stylus member 278 is directly coupled to the base member 276 and may include a first blade 297 and a second blade 299 configured to make orthogonal cuts in the sealing member 114 when the housing 258 is compressed with a driving force thereby impacting the cutting element 218. The stylus member 278 is thus driven into the sealing member 114. The driving force may be manually applied to the exterior 284 of the reduced-pressure interface 216 causing the housing 258 to collapse and thereby driving or pushing the cutting element 218 into the sealing member 114. In another embodiment, the driving force is applied by applying reduced pressure to the cavity 264 such that the cavity pressure ($P_c$) in the cavity 264 is less than a threshold pressure ($P_t$). When the cavity pressure ($P_c$) in the cavity 264 is less than the threshold pressure ($P_t$), the cavity wall portion 262 collapses and impacts the cutting element 218. With continued reduced pressure, a portion of the cutting element 218 is driven through the sealing member 114. The threshold pressure ($P_t$) is at least in part dependent on the type and thickness of material used for the housing 258. In the event reduced pressure is applied to the cavity 264, a tensile force 273 may be applied to the sealing member 114 causing the sealing member 114 to be pulled into the cavity 264. This movement helps the cutting element 218 to be driven into the sealing member 114.

As previously mentioned, the base member 276 may be only temporarily coupled to the housing 258. In one embodiment, the base member 276 and the stylus member 278 may be formed from a liquid soluble material such as a water soluble material adapted to allow the cutting element 118 to dissolve. The water soluble material may include at least one of the following: Polyvinyl alcohol (PVOH), polyvinyl pyrrolidone, hydroxyl and carboxyl modified cellulose, hydroxyl and carboxyl modified acrylics, starch, sugars (sucrose, glucose, fructose), weak acids (tartaric, citric, malic), salts (sodium chloride, sodium carbonate, sodium bicarbonate), polyethylene oxide (PEO), polyethylene glycol (PEG). The base member 276 and the stylus member 278 may dissolve as liquids are removed from the tissue site 102. Reduced pressure is applied to the reduced-pressure interface 216 typically causing liquids to be removed from the tissue site 102. After a sufficient amount of time, liquids removed from the tissue site 102 may cause the base member 276 and the stylus member 278 to substantially dissolve. The base member 276 and the stylus member 278 may dissolve within 2 minutes, 5 minutes, 8 minutes, 10 minutes, or another time period. As the base member 276 and the stylus member 278 are dissolved, the base member 276 and the stylus member 278 are removed by the reduced-pressure delivery conduit 110 with the liquids from the tissue site 102. While the base member 276 and the stylus member 278 may be dissolvable, it is worth noting that the conduit adapter 292, the adapter flange 294, and the tube extension 296 do not dissolve.

Once the base member 276 and the stylus member 278 have substantially dissolved, reduced pressure applied through the reduced-pressure interface 216 creates sufficient reduced pressure in the cavity 264 to pull a portion of the distribution manifold 112 into the cavity 264 and the primary lumen 142 of the reduced-pressure delivery conduit 110. The distribution manifold 112 abuts the distal end of the reduced-pressure delivery conduit 110 including the distal aperture 186 of the at least one sensing lumen 144. Allowing the distribution manifold 112 to completely abut the distal end of the reduced-pressure delivery conduit 110 may help ensure fluid isolation between each of the lumens in the reduced-pressure delivery conduit 110.

Figure 10:
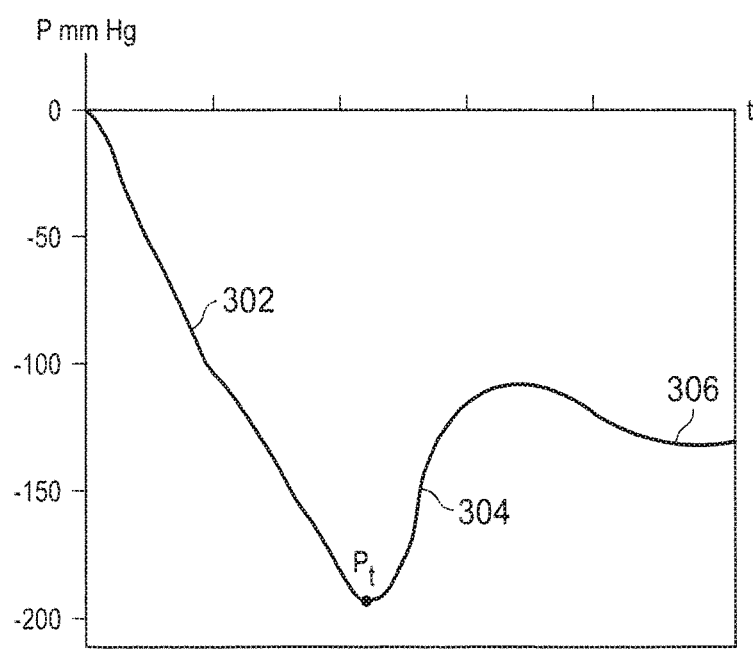
FIG. 10 is a schematic diagram of a representative pressure set-up pattern.

Referring now primarily to FIG. 10, a schematic diagram of a pressure set-up pattern is presented. The pressure set-up pattern may be a pre-determined pressure configuration. Pressure-detection sensors may communicate with a processing unit to monitor whether pressure signals received from a reduced-pressure interface follow or is consistent with the pressure set-up pattern. The pressure set-up pattern may be representative of whether a cutting element of the reduced-pressure interface has pierced a sealing member. The pressure set-up pattern may represent four main events. First, a period of sustained pressure decrease (reduced pressure increase) may be indicative of a period of time prior to the cutting element piercing the sealing member. This segment is shown generally by reference numeral 302. During this period of time, pressure is decreasing in a cavity of the reduced-pressure interface causing the cavity to collapse. Second, a threshold pressure ($P_t$) is reached and pressure increases (reduced pressure decreases) indicating that the cutting element has pierced the sealing member. This segment is generally shown by numeral 304. The pressure should increase as the pressure in the sealed space beneath the sealing member stabilizes. And third, a period of pressure stability is reached as shown generally as reference numeral 306.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An interface for treating a tissue site, the interface comprising:
   a housing, the housing comprising:
      a flange configured to be coupled to a sealing member, and
      a cavity wall forming a cavity, the cavity having a tissue-facing cavity opening;
   a conduit aperture through the cavity wall;
   a reduced-pressure delivery conduit configured to be coupled to the conduit aperture, the reduced-pressure delivery conduit comprising:
      a primary lumen configured to provide reduced pressure to the cavity and communicate exudate from the cavity, and
      at least one sensing lumen configured to communicate reduced pressure representative of the tissue site when fluid communication is established between the tissue site and the cavity; and
   a cutting element coupled to the housing proximate the tissue-facing cavity opening and configured to form an aperture in the sealing member establishing fluid communication between the tissue site and the cavity.

2. The interface of claim 1, wherein cutting element comprises a stylus having a leading edge, wherein the stylus is configured to perforate the sealing member to form an access aperture in the sealing member and to apply a tensile force on the access aperture.

3. The interface of claim 2, wherein a piercing length of the cutting element is less than 3 centimeters.

4. The interface of claim 2, wherein a piercing length of the cutting element is less than 2 centimeters.

5. The interface of claim 2, wherein the stylus has a first blade and a second blade configured to make orthogonal cuts in the sealing member.

6. The interface of claim 1, wherein the cutting element is releasably coupled to the housing.

7. The interface of claim 1, further comprising an attachment device coupled to a tissue-facing side of the flange, the attachment device configured to couple the housing to the sealing member.

8. The interface of claim 7, wherein the attachment device comprises an adhesive.

9. The interface of claim 1, wherein the cutting element is formed from a water soluble material.

10. The interface of claim 9, wherein the water soluble material comprises at least one of the following: Polyvinyl alcohol (PVOH), polyvinyl pyrrolidone, hydroxyl and carboxyl modified cellulose, hydroxyl and carboxyl modified acrylics, starch, a sugar, a weak acid, a salt, polyethylene oxide (PEO), polyethylene glycol (PEG).

11. The interface of claim 1, wherein the housing comprises a semi-rigid material that collapses when exposed to a pressure in the cavity that is less than a threshold pressure.

12. A system for treating a tissue site, the system comprising:
   a distribution manifold;
   a sealing member configured to cover the distribution manifold; and
   a reduced-pressure interface comprising:
      a housing having a flange configured to be coupled to the sealing member, and a cavity wall forming a cavity, the cavity having a tissue-facing cavity opening,
      a conduit aperture through the cavity wall,
      a reduced-pressure delivery conduit configured to be coupled to the conduit aperture, the reduced-pressure delivery conduit comprising:
         a primary lumen configured to provide reduced pressure to the cavity and communicate exudate from the cavity, and
         at least one sensing lumen configured to communicate reduced pressure representative of the tissue site when fluid communication is established between the tissue site and the cavity, and
      a cutting element coupled to the housing proximate the tissue-facing cavity opening and configured to form an aperture in the sealing member establishing fluid communication between the tissue site and the cavity.

13. The system of claim 12, wherein the cutting element comprises:
   a base member;
   a stylus member coupled to the base member, wherein the stylus member has a leading edge and is configured to perforate the sealing member to form the aperture in the sealing member and to apply a tensile force on the aperture.

14. The system of claim 13, wherein the stylus member has a first blade and a second blade configured to make orthogonal cuts in the sealing member.

15. The system of claim 12, wherein the distribution manifold has a thickness when subject to reduced pressure, wherein the cutting element has a piercing length, and wherein the piercing length is less than the thickness.

16. The system of claim 12, wherein the cutting element is formed from a water soluble material.

17. The system of claim 16, wherein the water soluble material comprises at least one Polyvinyl alcohol (PVOH), polyvinyl pyrrolidone, hydroxyl and carboxyl modified cellulose, hydroxyl and carboxyl modified acrylics, starch, a sugar, a weak acid, a salt, polyethylene oxide (PEO), or polyethylene glycol (PEG).

18. The system of claim 12, wherein the housing is made of a semi-rigid material that collapses when exposed to a pressure in the cavity that is less than a threshold pressure.

19. The system of claim 12, further comprising an instrumentation unit fluidly coupled to the at least one sensing lumen, wherein the instrumentation unit includes a microprocessor and is configured to:
   process a pressure signal representative of a pressure at a distal end of the at least one sensing lumen;

monitor the pressure signal; and issue an alert if the pressure signal does not follow a pattern of sustained decrease, increase, and stability within an application time period.

20. A method for treating a tissue site on a patient with reduced pressure, the method comprising:
   disposing a distribution manifold proximate to the tissue site;
   covering the distribution manifold and a portion of intact epidermis of the patient with a sealing member to form a sealed space;
   coupling a reduced-pressure interface to the sealing member;
   coupling a reduced-pressure source to the reduced-pressure interface;
   wherein the reduced-pressure interface comprises:
      a housing having a flange configured to be coupled to the sealing member, and a cavity wall forming a cavity, the cavity having a tissue-facing cavity opening,
      a conduit aperture through the cavity wall,
      a reduced-pressure delivery conduit coupled to the conduit aperture, the reduced-pressure delivery conduit comprising:
         a primary lumen configured to provide reduced pressure to the cavity and communicate exudate from the cavity, and
         at least one sensing lumen configured to communicate reduced pressure representative of the tissue site when fluid communication is established between the tissue site and the cavity, and
      a cutting element coupled to the housing proximate the tissue-facing cavity opening and configured to form an aperture in the sealing member establishing fluid communication between the tissue site and the cavity.

21. The method of claim 20, wherein coupling the reduced-pressure interface to the sealing member comprises using an attachment device of the reduced-pressure interface to adhere the reduced-pressure interface to the sealing member.

22. The method of claim 20, wherein the reduced-pressure interface is coupled to the sealing member with an adhesive.

23. The method of claim 20, wherein coupling the reduced-pressure source to the reduced-pressure interface comprises fluidly coupling a reduced-pressure delivery conduit to the reduced-pressure source and the reduced-pressure interface.

24. The method of claim 20, wherein coupling the reduced-pressure source to the reduced-pressure interface comprises fluidly coupling a reduced-pressure delivery conduit to the reduced-pressure source and the reduced-pressure interface; and further comprising applying reduced pressure through the reduced-pressure interface to create sufficient reduced pressure in the cavity of the housing to pull a portion of the distribution manifold into the housing such that the distribution manifold abuts a distal aperture of the at least one sensing lumen.

25. The method of claim 20, further comprising applying a driving force to the reduced-pressure interface of sufficient strength to cause the cutting element to perforate the sealing member.

26. The method of claim 25, wherein applying the driving force to the reduced-pressure interface comprises manually applying the driving force to an exterior of the reduced-pressure interface.

27. The method of claim 25, wherein the housing is formed of a semi-rigid material that collapses when under reduced pressure less than a threshold pressure, and wherein applying the driving force to the reduced-pressure interface comprises applying reduced pressure to collapse the housing and drive a portion of the cutting element through the sealing member.

28. The method of claim 20, wherein the cutting element is formed from a liquid soluble material; and further comprising providing reduced pressure to the reduced-pressure interface for a sufficient time after perforating the sealing member such that liquids are removed from the tissue site and such that the cutting element substantially dissolves.

29. The method of claim 20, wherein the cutting element comprises:
   a base member; and
   a stylus member coupled to the base member, wherein the stylus member has a leading edge configured to perforate the sealing member.

30. The method of claim 29, wherein the stylus member has a first blade and a second blade configured to make orthogonal cuts in the sealing member.

31. The method of claim 20, wherein the distribution manifold has a thickness when subject to reduced pressure, wherein the cutting element has a piercing length, and wherein the piercing length is less than the thickness.

32. The method of claim 20, wherein the cutting element is releasably coupled to the housing.

33. The method of claim 20, further comprising:
   monitoring a pressure through the at least one sensing lumen; and
   providing an indication if a pressure signal associated with the pressure does not follow a pressure set-up pattern.

* * * * *